(12) United States Patent
Milevski et al.

(10) Patent No.: US 10,049,184 B2
(45) Date of Patent: Aug. 14, 2018

(54) SOFTWARE APPLICATION TRANSMISSION VIA BODY INTERFACE USING A WEARABLE DEVICE IN CONJUNCTION WITH REMOVABLE BODY SENSOR ARRAYS SYSTEM AND METHOD

(71) Applicant: BRAGI GmbH, München (DE)

(72) Inventors: Veniamin Milevski, München (DE); Peter Vincent Boesen, München (DE)

(*) Notice: Subject to any disclaimer, the term of this patent is extended or adjusted under 35 U.S.C. 154(b) by 0 days.

(21) Appl. No.: 15/720,058

(22) Filed: Sep. 29, 2017

(65) Prior Publication Data

US 2018/0101656 A1 Apr. 12, 2018

Related U.S. Application Data

(60) Provisional application No. 62/405,524, filed on Oct. 7, 2016.

(51) Int. Cl.
*G06F 19/00* (2018.01)
*H04B 1/3827* (2015.01)
(Continued)

(52) U.S. Cl.
CPC ........ *G06F 19/3418* (2013.01); *A61B 5/0008* (2013.01); *A61B 5/02055* (2013.01);
(Continued)

(58) Field of Classification Search
CPC .... G06F 19/3418; G06F 3/011; G06F 1/1613; A61B 5/0008; A61B 5/02055;
(Continued)

(56) References Cited

U.S. PATENT DOCUMENTS 2,325,590 A 8/1943 Carlisle et al.
2,430,229 A 11/1947 Kelsey
(Continued)

FOREIGN PATENT DOCUMENTS

CN 204244472 U 4/2015
CN 104683519 A 6/2015
(Continued)

OTHER PUBLICATIONS

Wikipedia, "Wii Balance Board", "https://en.wikipedia.org/wik/Wii_Balance_Board", 3 pages, (Jul. 20, 2017).
(Continued)

*Primary Examiner* — Andrew Wendell
(74) *Attorney, Agent, or Firm* — Goodhue, Coleman & Owens, P.C.

(57) ABSTRACT

A method for communicating data from wearable devices, the method includes sensing data with a wearable sensor worn by an individual and communicating the data from the wearable sensor to an earpiece worn by the individual. The method may further include communicating software instructions for analyzing the data sensed with the wearable sensor from the wearable sensor to the earpiece. An earpiece includes an ear piece housing, a processor disposed within the ear piece housing, a speaker operatively connected to the processor, and a microphone operatively connected to the processor. The earpiece is configured to receive at the processor the software instructions for processing data collected from one or more remotely located sensor devices from the one or more remotely located sensor devices and to process the data according to the software instructions.

16 Claims, 4 Drawing Sheets

(51) Int. Cl.
  *H04B 5/00* (2006.01)
  *H04W 4/38* (2018.01)
  *A61B 5/00* (2006.01)
  *A61B 5/0205* (2006.01)
  *G06F 3/01* (2006.01)
  *G06Q 50/22* (2018.01)
  *G06F 1/16* (2006.01)
  *H04L 29/08* (2006.01)

(52) U.S. Cl.
  CPC ............ *A61B 5/6815* (2013.01); *G06F 3/011* (2013.01); *G06F 1/1613* (2013.01); *G06Q 50/22* (2013.01); *H04L 29/08* (2013.01)

(58) Field of Classification Search
  CPC ...... A61B 5/6815; H04L 29/08; G06Q 50/22; H04B 5/0043; H04B 1/385; H04B 2001/3872; H04B 5/0006; H04W 4/80; H04W 4/38
  See application file for complete search history.

(56) References Cited

U.S. PATENT DOCUMENTS

| | | | |
|---|---|---|---|
| 3,047,089 A | 7/1962 | Zwislocki |
| D208,784 S | 10/1967 | Sanzone |
| 3,586,794 A | 6/1971 | Michaelis |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| D601,134 S | 9/2009 | Elabidi et al. |
| 7,825,626 B2 | 11/2010 | Kozisek |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| D666,581 S | 9/2012 | Perez |
| 8,300,864 B2 | 10/2012 | Müllenborn et al. |
| 8,406,448 B2 | 3/2013 | Lin |
| 8,436,780 B2 | 5/2013 | Schantz et al. |
| D687,021 S | 7/2013 | Yuen |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| 9,544,689 B2 | 1/2017 | Fisher et al. |
| D788,079 S | 5/2017 | Son et al. |
| 9,818,005 B2 * | 11/2017 | Yeager ............... G06K 7/10158 |

(56) References Cited

U.S. PATENT DOCUMENTS

| | | |
|---|---|---|
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2008/0076972 A1 | 3/2008 | Dorogusker et al. |
| 2008/0090622 A1 | 4/2008 | Kim et al. |
| 2008/0146890 A1 | 6/2008 | LeBoeuf et al. |
| 2008/0187163 A1 | 8/2008 | Goldstein et al. |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2010/0033313 A1 | 2/2010 | Keady et al. |
| 2010/0169075 A1* | 7/2010 | Raffa ................. G06F 17/2775 704/9 |
| 2010/0203831 A1 | 8/2010 | Muth |
| 2010/0210212 A1 | 8/2010 | Sato |
| 2010/0320961 A1 | 12/2010 | Castillo et al. |
| 2011/0018731 A1* | 1/2011 | Linsky .................. G06F 1/163 715/863 |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2012/0057740 A1 | 3/2012 | Rosal |
| 2013/0316642 A1 | 11/2013 | Newham |
| 2013/0343585 A1* | 12/2013 | Bennett ................ H04R 25/554 381/315 |
| 2013/0346168 A1 | 12/2013 | Zhou et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0110587 A1 | 4/2015 | Hori |
| 2015/0148989 A1 | 5/2015 | Cooper et al. |
| 2015/0245127 A1 | 8/2015 | Shaffer |
| 2015/0310720 A1* | 10/2015 | Gettings ............... G08B 29/188 340/540 |
| 2015/0373467 A1 | 12/2015 | Gelter |
| 2015/0373474 A1 | 12/2015 | Kraft et al. |
| 2016/0033280 A1 | 2/2016 | Moore et al. |
| 2016/0072558 A1 | 3/2016 | Hirsch et al. |
| 2016/0073189 A1 | 3/2016 | Lindén et al. |
| 2016/0125892 A1 | 5/2016 | Bowen et al. |
| 2016/0352818 A1* | 12/2016 | Han ....................... G06F 9/4893 |
| 2016/0353196 A1 | 12/2016 | Baker et al. |
| 2016/0360350 A1 | 12/2016 | Watson et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0065228 A1* | 3/2017 | Hirano .................. A61B 5/721 |
| 2017/0078780 A1 | 3/2017 | Qian et al. |
| 2017/0078785 A1 | 3/2017 | Qian et al. |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0119318 A1* | 5/2017 | Shay .................... A61B 5/7285 |
| 2017/0127168 A1 | 5/2017 | Briggs et al. |
| 2017/0142511 A1 | 5/2017 | Dennis |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251933 A1 | 9/2017 | Braun et al. |

(56) References Cited

U.S. PATENT DOCUMENTS

| | | | |
|---|---|---|---|
| 2017/0257698 A1 | 9/2017 | Boesen et al. | |
| 2017/0263236 A1 | 9/2017 | Boesen et al. | |
| 2017/0273622 A1 | 9/2017 | Boesen | |

FOREIGN PATENT DOCUMENTS

| | | | |
|---|---|---|---|
| CN | 104837094 A | 8/2015 | |
| EP | 1469659 A1 | 10/2004 | |
| EP | 1017252 A3 | 5/2006 | |
| EP | 2903186 A1 | 8/2015 | |
| GB | 2074817 | 4/1981 | |
| GB | 2508226 A | 5/2014 | |
| WO | 2008103925 A1 | 8/2008 | |
| WO | 2007034371 A3 | 11/2008 | |
| WO | 2011001433 A2 | 1/2011 | |
| WO | 2012071127 A1 | 5/2012 | |
| WO | 2013134956 A1 | 9/2013 | |
| WO | 2014046602 A1 | 3/2014 | |
| WO | 2014043179 A3 | 7/2014 | |
| WO | 2015061633 A2 | 4/2015 | |
| WO | 2015110577 A1 | 7/2015 | |
| WO | 2015110587 A1 | 7/2015 | |
| WO | 2016032990 A1 | 3/2016 | |

OTHER PUBLICATIONS

Akkermans, "Acoustic Ear Recognition for Person Identification", Automatic Identification Advanced Technologies, 2005 pp. 219-223.
Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected-The personalized digital assistant", "http://bmwblog.com/2016/01/05/bmw-introduces-bmw-connected-the-personalized-digital-assistant", (Jan. 5, 2016).
Bragi Is On Facebook (2014).
Bragi Update—Arrival of Prototype Chassis Parts—More People—Awesomeness (May 13, 2014).
Bragi Update—Chinese New Year, Design Verification, Charging Case, More People, Timeline(Mar. 6, 2015).
Bragi Update—First Sleeves From Prototype Tool—Software Development Kit (Jun. 5, 2014).
Bragi Update—Let's Get Ready to Rumble, A Lot to Be Done Over Christmas (Dec. 22, 2014).
Bragi Update—Memories From Apr.—Update on Progress (Sep. 16, 2014).
Bragi Update—Memories from May—Update on Progress—Sweet (Oct. 13, 2014).
Bragi Update—Memories From One Month Before Kickstarter—Update on Progress (Jul. 10, 2014).
Bragi Update—Memories From the First Month of Kickstarter—Update on Progress (Aug. 1, 2014).
Bragi Update—Memories From the Second Month of Kickstarter—Update on Progress (Aug. 22, 2014).
Bragi Update—New People ©Bragi—Prototypes (Jun. 26, 2014).
Bragi Update—Office Tour, Tour to China, Tour to CES (Dec. 11, 2014).
Bragi Update—Status on Wireless, Bits and Pieces, Testing-Oh Yeah, Timeline(Apr. 24, 2015).
Bragi Update—The App Preview, The Charger, The SDK, Bragi Funding and Chinese New Year (Feb. 11, 2015).
Bragi Update—What We Did Over Christmas, Las Vegas & CES (Jan. 19, 2014).
Bragi Update—Years of Development, Moments of Utter Joy and Finishing What We Started(Jun. 5, 2015).
Bragi Update—Alpha 5 and Back to China, Backer Day, on Track(May 16, 2015).
Bragi Update—Beta2 Production and Factory Line(Aug. 20, 2015).
Bragi Update—Certifications, Production, Ramping Up.
Bragi Update—Developer Units Shipping and Status(Oct. 19, 2015).
Bragi Update—Developer Units Started Shipping and Status (Oct. 19, 2015).
Bragi Update—Developer Units, Investment, Story and Status(Nov. 2, 2015).
Bragi Update—Getting Close(Aug. 16, 2015).
Bragi Update—On Track, Design Verification, How It Works and What's Next(Jul. 15, 2015).
Bragi Update—On Track, On Track and Gems Overview.
Bragi Update—Status on Wireless, Supply, Timeline and Open House@Bragi(Apr. 1, 2015).
Bragi Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, Californa (2017).
International Search Report & Written Opinion, PCT/EP2016/070231 (Nov. 18, 2016).
Last Push Before the Kickstarter Campaign Ends on Monday 4pm CET (Mar. 28, 2014).
Nigel Whitfield: "Fake tape detectors, 'from the stands' footie and UGH? Internet of Things in my set-top box"; http://www.theregister. co.uk/2014/09/24/ibc_round_up_object_audio_dlna jot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometrics.html", 4 pages (Jul. 28, 2015).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for The Dash (Feb. 12, 2014).
Stretchgoal—Windows Phone Support (Feb. 17, 2014).
The Dash + The Charging Case & The Bragi News (Feb. 21, 2014).
The Dash-A Word From Our Software, Mechanical and Acoustics Team + An Update (Mar. 11, 2014).
Update From Bragi—$3,000,000—Yipee (Mar. 22, 2014).
Wertzner et al., "Analysis of fundamental frequency, jitter, shimmer and vocal intensity in children with phonological disorders", V.71, No. 5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).

* cited by examiner

SOFTWARE APPLICATION TRANSMISSION VIA BODY INTERFACE USING A WEARABLE DEVICE IN CONJUNCTION WITH REMOVABLE BODY SENSOR ARRAYS SYSTEM AND METHOD

RELATED APPLICATIONS

This application claims priority to U.S. Provisional Patent Application No. 62/405,524, filed Oct. 7, 2016, hereby incorporated by reference in its entirety.

FIELD OF THE INVENTION

The present invention relates to wearable devices. More particularly, but not exclusively, the present invention relates to ear pieces and other sensors worn on the body for use in capturing multipoint data.

BACKGROUND

Current and upcoming technology is limited by the available methods for sensor location on the body of the user. Multiple schemes have been devised, but face ongoing issues with power supply as well as processing capability. What is needed is a new way to localize sensors on the body of the user to provide multipoint data capture for transmission wirelessly to worn devices that can process the data and incorporate that processed data into higher level schemes.

SUMMARY

Therefore, it is a primary object, feature, or advantage to improve over the state of the art.

It is a further object, feature, or advantage to provide for processing of body worn sensors using a wearable receptor device.

It is a still further object, feature, or advantage to communicate operational software from sensors associated with body worn accessories to a wearable receptor device such as an ear piece.

Another object, feature, or advantage is to reduce the amount of processing power and/or battery associated with body worn accessories in or to allow for reduced size and/or energy consumption.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an objects, features, or advantages stated herein.

According to one aspect, a method for communicating data from wearable devices is provided. The method includes sensing data with a wearable sensor worn by an individual and communicating the data from the wearable sensor to an earpiece worn by the individual. The method may further include communicating software instructions for analyzing the data sensed with the wearable sensor from the wearable sensor to the earpiece. The communication linkage may be a galvanic communication linkage or other wireless communication linkage.

According to another aspect, a system includes a wearable device comprising a sensor and software instructions stored on a machine readable storage medium for processing data collected by the sensor. The system further includes an earpiece having an ear piece housing, a processor disposed within the ear piece housing, a speaker operatively connected to the processor, and a microphone operatively connected to the processor. The earpiece may be configured to communicate with the wearable device to collect data from the wearable device, to receive the software instructions from the wearable device, and to process the data at the processor using the software instructions. The earpiece may be further configured to prompt a user to authorize the software instructions from the wearable device such as before receiving the software instructions and/or before processing the software instructions.

According to another aspect, a system includes a first wearable device comprising a sensor and software instructions stored on a machine readable storage medium for processing data collected by the sensor. A second wearable device includes a wearable device housing and a processor disposed within the wearable device housing. The second wearable device is configured to communicate with the first wearable device to collect data from the first wearable device, to receive the software instructions from the first wearable device, and to process the data at the processor of the second wearable device using the software instructions. The second wearable device may be configured to prompt a user to authorize the software instructions from the first wearable device. The second wearable device may include a speaker operatively connected to the processor and a microphone operatively connected to the processor. The second wearable device may be an earpiece or a set of earpieces.

DETAILED DESCRIPTION OF THE DISCLOSURE

Multiple sensors may be incorporated into clothing or other body worn accessories including jewelry items such as watches. These accessories are equipped with operational software that can be transmitted galvanically, wirelessly, or otherwise to the receptor units in the ear for sophisticated analysis, processing and transmission of the processed data. These data systems are unable to process or fully process by themselves, and are reliant upon powered devices for full implementation. The signals generated can be transmitted to the receptor devices through wireless schemes, such as electromagnetic fields or other low power wireless networks.

The data can then be processed using a built in software program that is in itself, transmitted to the wearable receptor device that provides the processing capability for the remote sensor array.

Thus, software for analysis may reside with the remote sensor array of the wearable device. The software may be transmitted via wireless low power transmission schemes to the wearable device (such as an earpiece which is capable of processing. This communication may be via galvanic transmission or other very low power transmission schemes. This allows for the ready exchange and modulation of the programming based upon the array presented in the remote wearable location. Authorization of a transmitted applet to the device may be requested of the user prior to any processing at the wearable device.

Figure 1:
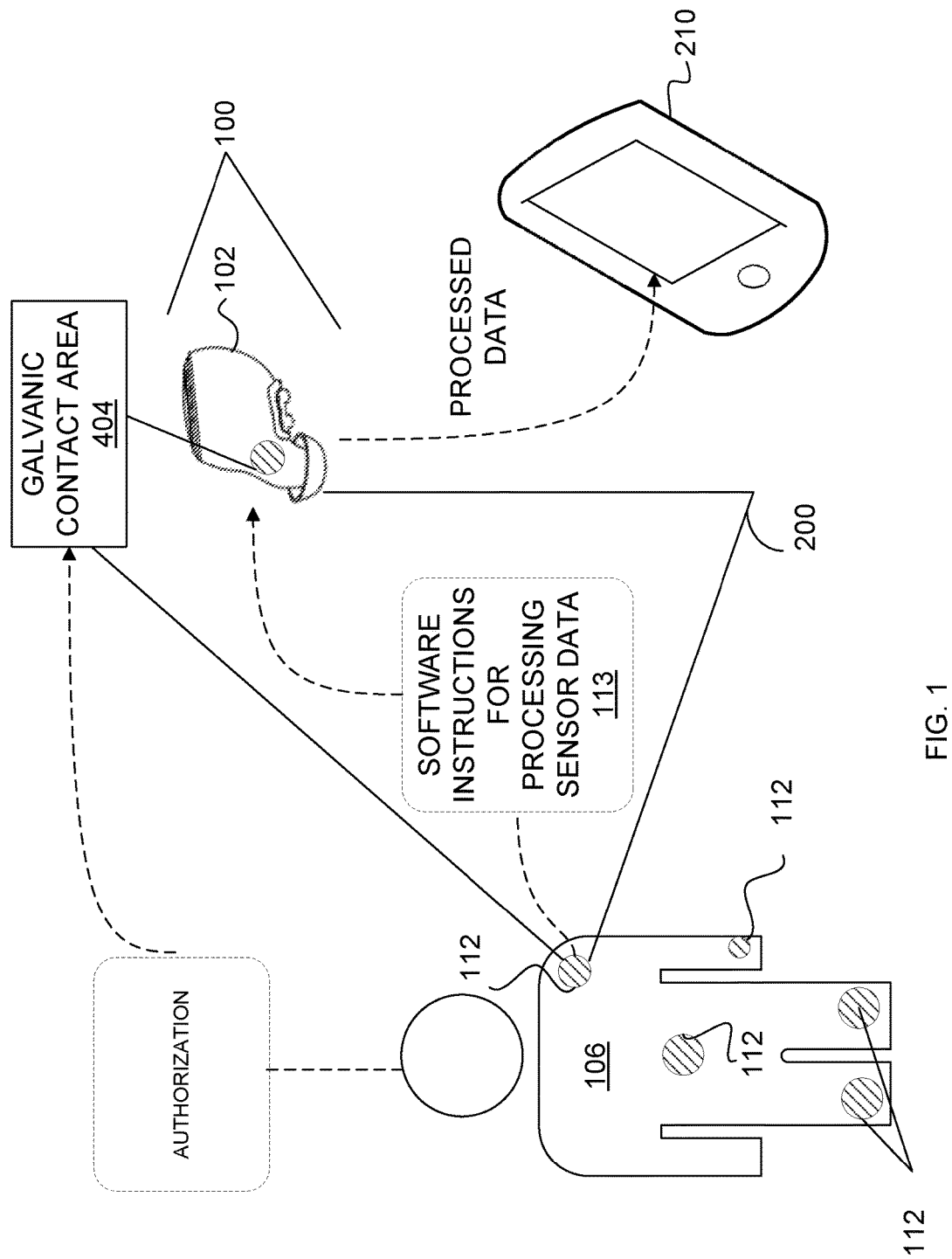
FIG. 1 is a pictorial representation of a communication system in accordance with an illustrative embodiment.

One embodiment of the illustrative embodiments provides a receptor device such as an earpiece 100 having an earpiece housing 102, as shown in FIG. 1. The earpiece 100 may be important to a user for business, exercise, or personal activities. The earpiece housing 102 includes a frame to fit substantially within the ears of the user. The earpiece housing 102 may be composed of a single structure or multiple, interconnected structures. The earpieces 100 may also contain sensors to perform sensor measurements for the user to read any number of user biometrics. These user biometrics may be analyzed to include measuring deviations or changing sensor measurements over time, identifying trends of the sensor measurements, and comparing the sensor measurements to control data for the user. The biometrics may also be used A number of different body worn devices, or sensor devices 112 may be present on the body of a person 106 or otherwise associated with the person 106. These body worn devices may include any number of different sensing technologies for any number of different applications or purposes. This may include implantable as well as other body worn devices. Preferably these sensor devices 112 may have low power requirements and limited or no processing capabilities in order to reduce size, complexity, cost, power requirements, or other factors. A galvanic signal 200 may be used to communicate data from one or more sensor devices 112 to a galvanic contact area 404 of an earpiece 100. Galvanic communication involves the use of the human body as a transmission medium for electrical signals. Galvanic communication may occur via many embodiments, including but not limited to wireless intra-body communications, biomedical monitoring, and supplying power for implants. Galvanic communication may be used to communicate information between a wearable device having one or more sensor devices 112 and the wearable device 100 such as an earpiece. The earpiece 100 may then communicate across other communication channels or with other devices such as a computing device 210 such as a mobile phone. Information from the sensor devices 112 may be used for any number of different purposes including for identifying a person, an article of clothing or other object associated with the person, collecting health data about the person, including activity of the user such as exercise or other movement, or any number of different types of monitoring such as may be performed with a wearable device.

The sensor devices 112 may contain software instructions for processing of sensor data. These software instructions may be conveyed to the receptor device such as the earpiece 100. Thus, instead of each sensor device 112 performing its own data processing, the earpiece 100 may perform processing for many different earpieces according to different instruction sets from different sensor devices 112. The software instructions may take any number of forms. For example, in some embodiments an identifier is provided by the sensor devices 112 which the receptor device or earpiece 100 may perform a lookup operation either from local storage or remote storage in order to obtain the processing instructions. In other embodiments, the instructions themselves form a part of an applet which is communicated from the sensor devices 112 to the receptor device or earpiece 100 for execution. Any number of different types of wearable devices 112 or wearable sensor devices 112 may be present. The wearable sensor devices 112 may be located on any part of the user's body or on a device adjacent to or coupled to the user's body. The sensor devices 112 that may be part of this galvanic communication system may be incorporated on the wireless earpieces or other receptor device, or in a separate location on the user. The sensor devices 112 may be used to sense directly or indirectly user biometrics, including but not limited to pulse rate, blood pressure, blood oxygenation, temperature, calories expended, blood or sweat chemical content, voice and audio input, impact levels, and orientation (e.g., body, head, etc.). The sensor devices 112 may also determine the user's location, position, velocity, impact levels, and so forth. The sensor devices 112 may also receive user input and convert the user input into commands or selections made across personal devices of the personal area network. For example, the user input detected by the wireless earpieces may include voice commands, head motions, finger taps, finger swipes, motions or gestures, or other user inputs sensed by the wireless earpieces.

Many different types of sensor devices 112 may be used for galvanic communication, including but not limited to biomedical sensors worn on the outside of the body such as heart rate monitors; contact lenses embedded with a microchip; and digital tattoos which may come in the form of a transdermal patch. Galvanically communicating sensors may also include an adhesive patches for monitoring concussions; electronic pills; ingestible biomedical sensors; microneedle drug delivery systems; dietary spectrometer sensors; ultraviolet light exposure sensors; cerebral pressure sensors. Implantable galvanically communicating sensors may include aneurism monitors, brain sensors, blood analyzer chips, pressure sensors, skin sensors, drug delivery devices, pressure sensor detectors for damaged nerves, endoscope probes, insulin micro-pumps, microsurgical tools, and sensors for cardiac damage.

One galvanically communicating embodiment involves sensors sending electromagnetic signals through the biological tissues such as the skin, fat, bone, muscle, or other human tissue. In selecting a biological tissue to send the electromagnetic signal through, the signal transmission distance and the potential signal distribution of each tissue may be taken into consideration. By applying an electrical signal between a pair of transmitting electrodes, an electrical field is established. This electrical field may then be received by a pair of receiving electrodes.

A galvanic contact area 404 may be located between the sensor and the biological tissue to allow for enhanced communication of the electromagnetic or electrical signals. The galvanic contact area 404 may be used to assist in conducting signals to and from one or more earpieces and one or more other body worn wearable devices or sensors. It should be appreciated that where it is used, the galvanic contact area 404 may be placed in any number of different locations on the earpieces 100 which would be in contact with an individual wearing the earpiece 100. That which is shown is merely representative.

Figure 2:
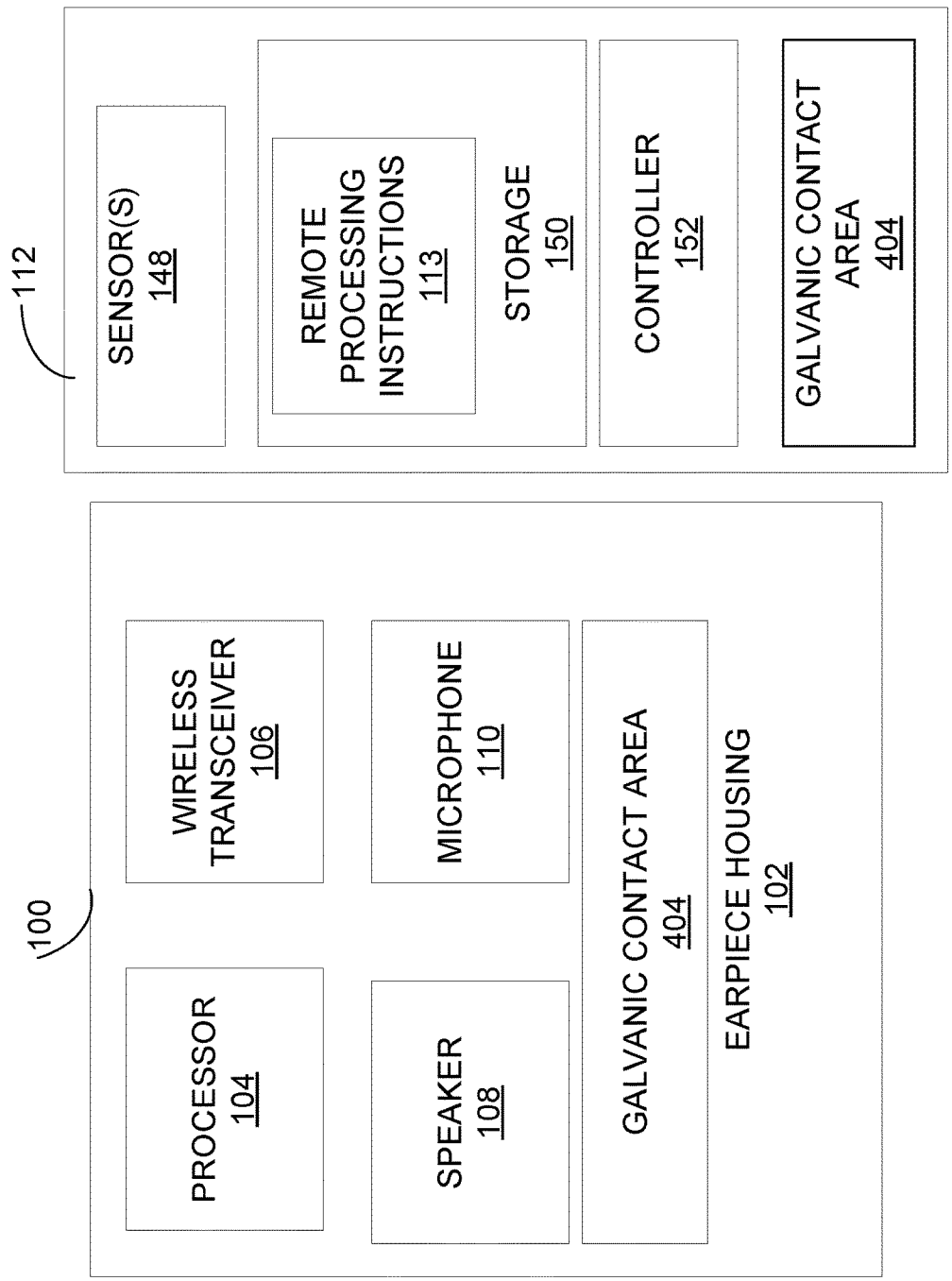
FIG. 2 is a block diagram of receptor devices and sensor devices.

As shown in FIG. 2, the system also includes a processor 104 disposed within the housing 102 of the receptor device or earpiece. The processor 104 may be a microprocessor, a digital signal processor, an application-specific integrated circuit (ASIC), a central processing unit, combination thereof, or another device suitable for controlling an electronic device including one or more hardware and software elements, executing software, instructions, programs, and applications, converting and processing signals and information, and performing other related tasks. Where the receptor device is an earpiece other components may include one or more speakers 108 and one or more microphones 110.

A galvanic contact area 404 is shown which may in operative communication with the wearable sensor 112. The wearable sensor device 112 may include one or more sensors 148 such as those previously described for detecting physiological or biometric information, movement or other activity, or state or condition of a device or a person. Storage 150 is shown which may be any type of memory or other storage. Remote processing instructions 113 may be stored within the storage. A controller 152 is shown which may be electrically connected to the sensors 148, the storage 150, and the galvanic contact area 404. The controller 152 may be a microprocessor, a digital signal processor, an application-specific integrated circuit (ASIC), a central processing unit, combination thereof, or other electronics for controlling the sensor device 112 and conveying remote processing instructions 113 to the receptor device 102.

Figure 3:
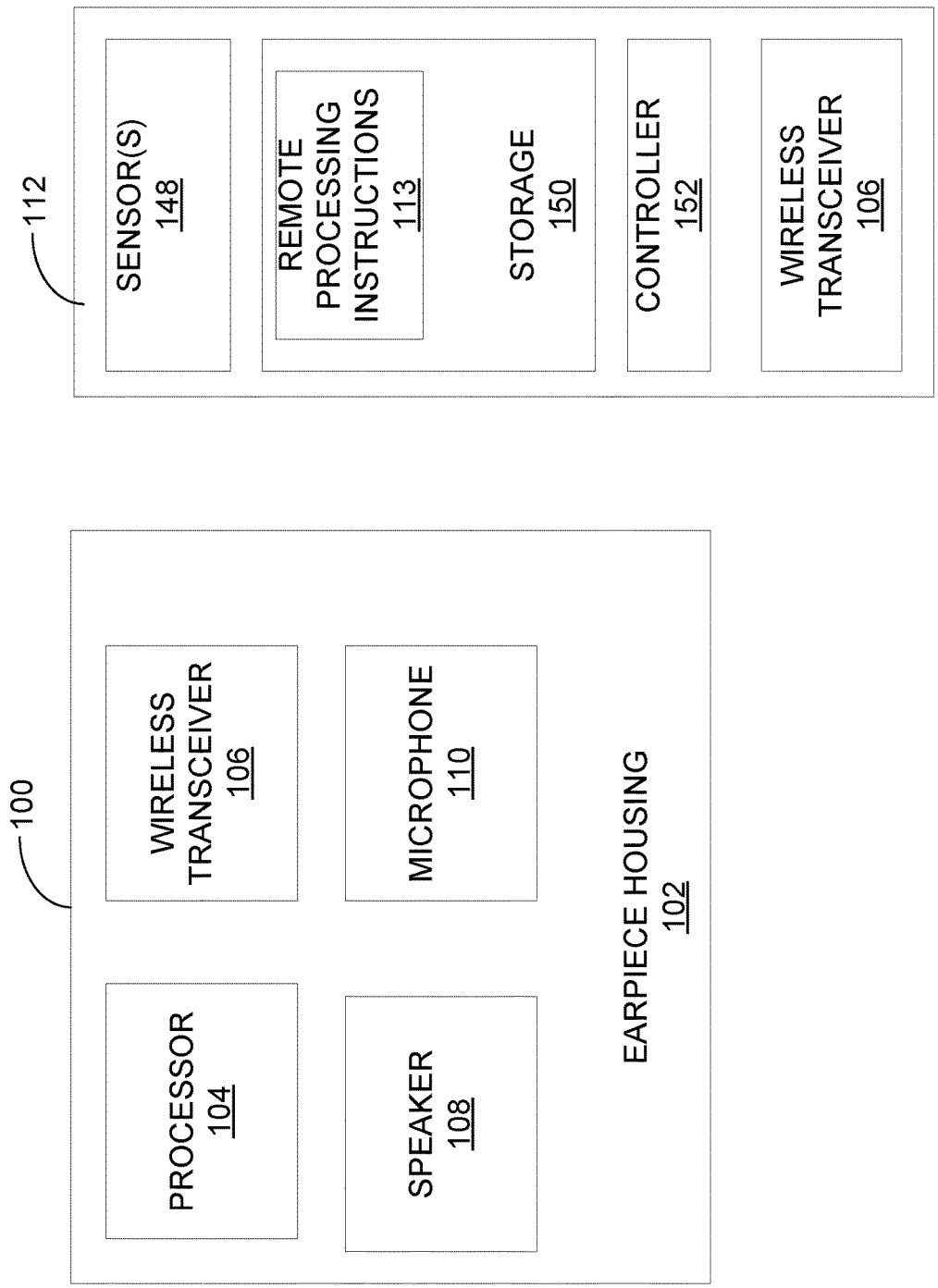
FIG. 3 is another block diagram of receptor devices and sensor devices.

FIG. 3 illustrates another configuration for the earpiece 100 and sensor device 112. As shown in FIG. 3, one or more wireless transceivers 106 may also be present. The wireless transceiver 106 may include a Bluetooth or Bluetooth Low Energy transceiver (BLE) 106 or other type of wireless transceiver. In addition, or alternatively, the earpiece may include circuitry for sending and receiving galvanically, a magnetic induction transceiver for communicating through magnetic induction, or other types of transceivers for communicating with other devices.

Figure 4:
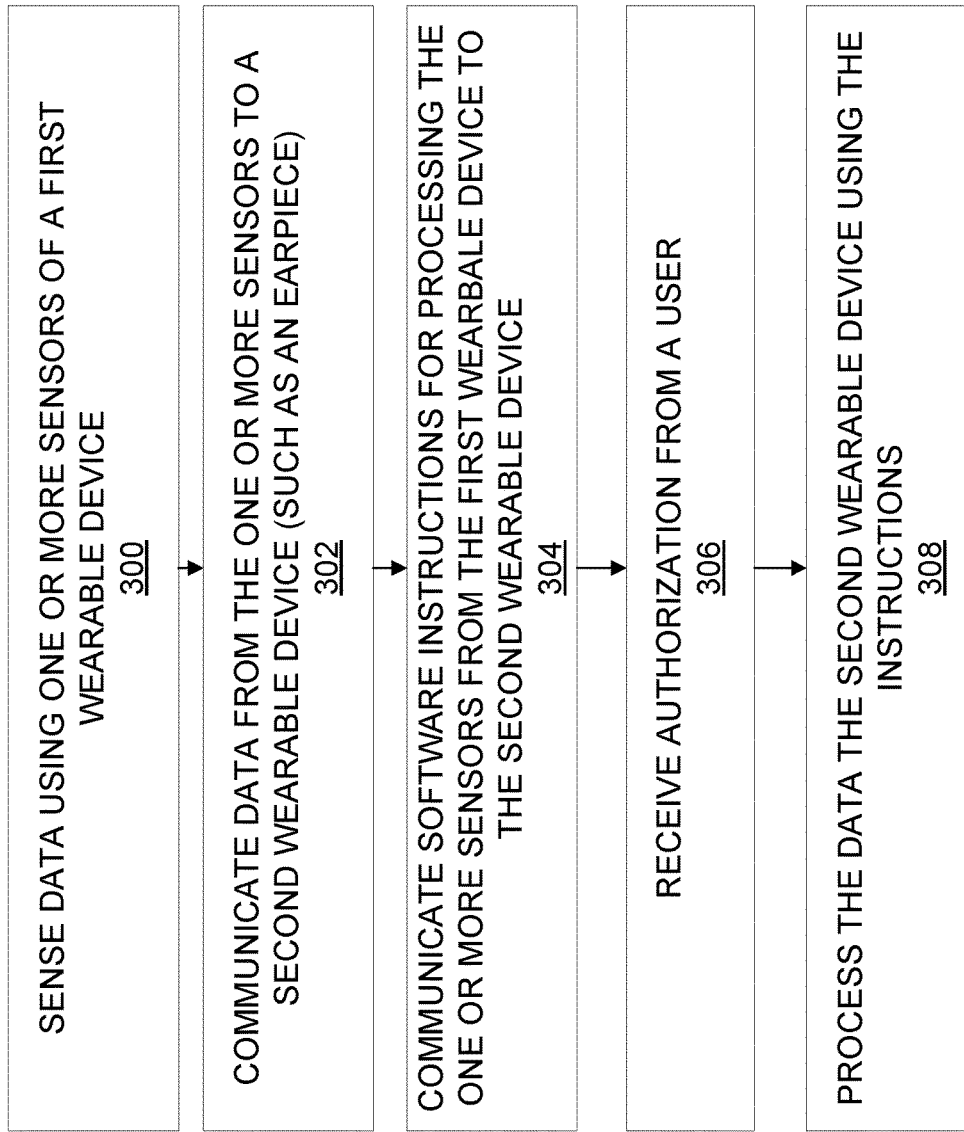
FIG. 4 is a flowchart of one method for use with wearable devices.

FIG. 4 illustrates one example of a methodology. In step 300, data is sensed using one or more sensors of a first wearable device. The data is then communicated from the one or more sensors to a second wearable device or receptor device such as an earpiece. In addition, software instructions are communicated to the second wearable device or receptor device for processing the sensor data from the first wearable device. In step 306, a user may provide authorization to allow the software instructions to be executed on the first wearable device. The user may be prompted to provide authorization, the user may provide pre-authorization, or other methods of authorization may be used. In step 308, the data is processed at the second wearable device using the instructions.

It is to be understood that a receptor device may also be a sensor device. For example, in a system where two earpieces are present, each earpiece could service as a receptor device or a sensor device. Thus, the earpiece could communicate processing instructions to a receptor device, or the earpiece could perform processing on data from sensor devices based on instructions for performing processing received from the sensor devices.

Therefore, various methods, systems, and apparatus have been shown and described. It is to be understood that numerous variations, options, and alternatives are contemplated. This includes variations in the configuration of different devices, the manner in which data is communicated between receptor and sensor devices, the manner in which instructions are communicated between receptor and sensor devices, and other options, variations, and alternatives.

What is claimed is:

1. A method for communicating data from wearable devices, the method comprising:
   sensing data with a wearable sensor worn by an individual;
   communicating the data from the wearable sensor to an earpiece worn by the individual;
   communicating software instructions for analyzing the data sensed with the wearable sensor from the wearable sensor to the earpiece; and
   analyzing the data sensed with the wearable sensor at a processor of the earpiece using the software instructions.

2. The method of claim 1 wherein the communicating is galvanically communicating.

3. The method of claim 2 wherein the wearable sensor is in contact with skin of the individual.

4. The method of claim 3 wherein the earpiece comprises a galvanic contact area for positioning against skin of a user.

5. The method of claim 1 wherein the communicating is wirelessly communicating.

6. The method of claim 1 further comprising receiving authorization from the individual to execute the software instructions on the earpiece prior to analyzing the data sensed with the wearable sensor.

7. The method of claim 1 further comprising wirelessly communicating the data from the earpiece to a computing device.

8. The method of claim 7 wherein the computing device is a mobile device.

9. The method of claim 8 wherein the mobile device is a mobile phone.

10. An earpiece comprising:
    an ear piece housing;
    a processor disposed within the ear piece housing;
    a speaker operatively connected to the processor;
    a microphone operatively connected to the processor;
    wherein the earpiece is configured to receive at the processor software instructions for processing data collected from one or more remotely located sensor devices from the one or more remotely located sensor devices and to process the data according to the software instructions.

11. The earpiece of claim 10 further comprising a wireless transceiver disposed within the ear piece housing and wherein the software instructions for processing the data and the data collected from the one or more remotely located sensor devices is received through the wireless transceiver.

12. The earpiece of claim 10 wherein the earpiece is configured to communicate with the one or more remotely located sensor device through a galvanic linkage.

13. A system comprising:
    a first wearable device comprising a sensor and software instructions stored on a machine readable storage medium for processing data collected by the sensor;
    a second wearable device comprising:
        a wearable device housing;
        a processor disposed within the wearable device housing;
    wherein the second wearable device is configured to communicate with the first wearable device to collect data from the first wearable device, to receive the software instructions from the first wearable device, and to process the data at the processor of the second wearable device using the software instructions.

14. The system of claim 13 wherein the second wearable device is configured to prompt a user to authorize the software instructions from the first wearable device.

15. The system of claim 13 wherein the second wearable device further comprises a speaker operatively connected to the processor and a microphone operatively connected to the processor.

16. The system of claim 15 wherein the second wearable device is an earpiece.

* * * * *